United States Patent [19]
Fields

[11] Patent Number: 5,776,096
[45] Date of Patent: Jul. 7, 1998

[54] DUAL LUMEN VASCULAR CATHETER WITH EXPANDING SIDE PORTAL

[75] Inventor: Charles Bruce Fields, Pittsburg, Calif.

[73] Assignee: HDC Corporation, San Jose, Calif.

[21] Appl. No.: 660,020

[22] Filed: Jun. 6, 1996

[51] Int. Cl.$^6$ .................................................. A61M 3/00
[52] U.S. Cl. ........................ 604/43; 604/280; 604/246
[58] Field of Search ............................ 604/39, 43, 160, 604/244, 246, 247, 256, 264, 280, 283

[56] References Cited

U.S. PATENT DOCUMENTS

| | | | |
|---|---|---|---|
| 4,445,897 | 5/1984 | Ekbladh et al. | 604/43 |
| 4,895,561 | 1/1990 | Mahurkar | 604/43 |
| 4,973,319 | 11/1990 | Melsky | 604/247 |
| 4,995,863 | 2/1991 | Nichols et al. | 604/247 |
| 5,030,210 | 7/1991 | Alchas | 604/247 |
| 5,147,318 | 9/1992 | Hohn | 604/280 |
| 5,147,332 | 9/1992 | Moorehead | 604/247 |
| 5,250,034 | 10/1993 | Appling et al. | 604/247 |
| 5,348,536 | 9/1994 | Young et al. | 604/43 |
| 5,357,961 | 10/1994 | Fields et al. | 128/658 |
| 5,360,414 | 11/1994 | Yarger | 604/43 |
| 5,389,087 | 2/1995 | Miraki | 604/247 |
| 5,460,618 | 10/1995 | Harreld | 604/264 |

Primary Examiner—Mark Bockelman
Assistant Examiner—Deborah Blyveis
Attorney, Agent, or Firm—Lyon & Lyon LLP

[57] ABSTRACT

A dual lumen vascular catheter with expanding side portal includes a cylindrical tubing with one or more lumens inside. An effusion portal is located on the side of the tubing at an end of one lumen. The portal is oval-shaped, with an open-ended slit connected to an end of the oval opening. The slit is thereby expandable, allowing for vacuum relief during aspiration of blood in the event that the catheter is lodged with the portal pressed against an inner wall of the vein.

14 Claims, 2 Drawing Sheets

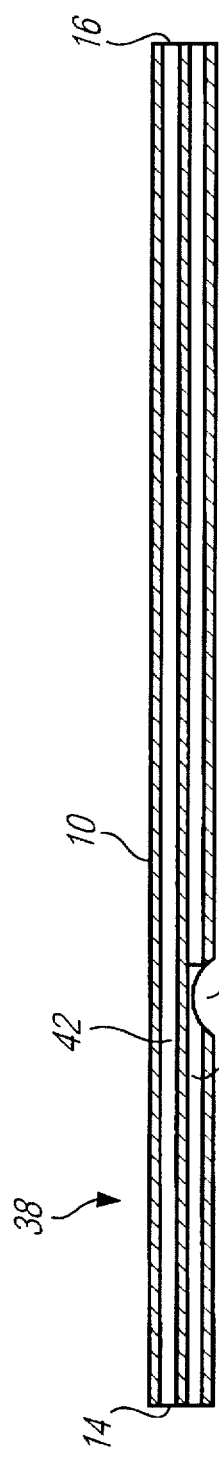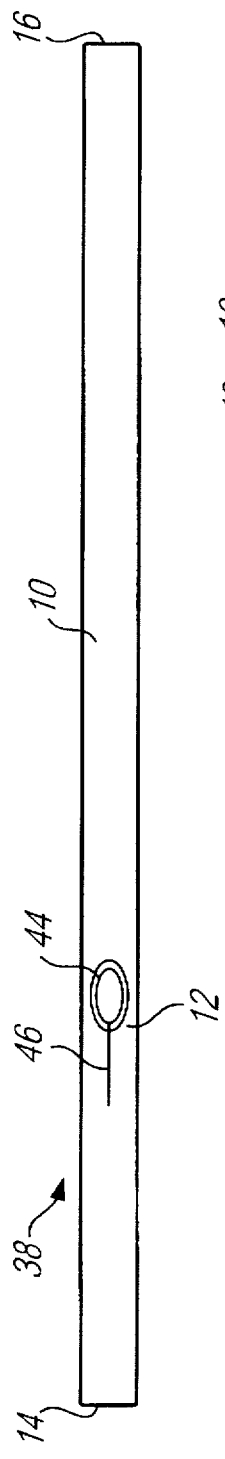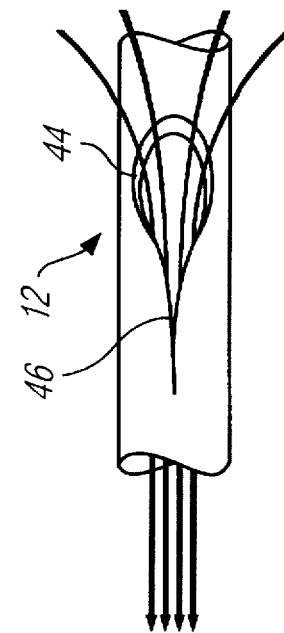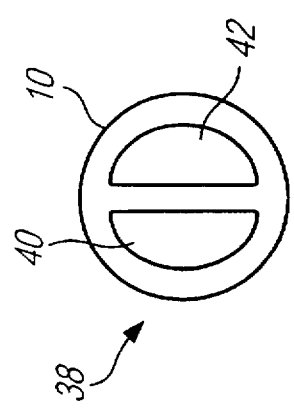

DUAL LUMEN VASCULAR CATHETER WITH EXPANDING SIDE PORTAL

BACKGROUND OF THE INVENTION

1. Field of the Invention

The field of the present invention is vascular catheters.

2. Background

Peripherally inserted central catheters (known as "PICCs") are commonly used to access the vascular system to deliver intravenous drugs such as therapeutic agents. An example of such a peripherally inserted catheter is disclosed in U.S. Pat. No. 5,357,961, which is assigned to the same assignee as the present invention. U.S. Pat. No. 5,357,961 is hereby incorporated by reference in its entirety.

Generally, peripherally inserted catheters are either single or dual lumen catheters. In dual lumen catheters, it is often necessary to delineate each lumen for individual medicines as it may be undesirable to mix the agents. Once a lumen has been dedicated to a certain purpose, it generally remains unusable for incompatible therapies during the indwelling period. Additionally, when one of the lumens of a dual lumen catheter is used for blood-drawing purposes, it is desirable to use a lumen of large enough diameter to ease blood flow and prevent damage to the blood sample. Thus, dual lumen vascular catheters are often fabricated with one lumen larger than the other, the larger lumen being used for blood sampling, the smaller lumen being used for delivering infusates. However, smaller lumens present problems during use. One significant problem is that more viscous infusates tend to have reduced flow rates with smaller lumens. However, it is advantageous for flow rates in each lumen to be comparable. It is also advantageous to have the ability to safely take a blood sample from either lumen of the dual lumen catheter should it become necessary.

In an equal-lumen design, it is generally desirable to have the lumens discharge their contents from staggered locations, rather than both from the tip of the catheter, so as to avoid mixture of infusates within the patient. Thus, one lumen discharges its contents from an opening at the distal tip (the end furthest from the point of insertion into the patient) of the catheter. The other lumen discharges its contents or draws a blood sample from a side effusion portal proximal to the distal end. The distal lumen is generally preferred for long-term procedures that cannot be interrupted such as central venous pressure monitoring. The proximal lumen is then free to use for drawing blood if necessary. However, drawing blood samples is more difficult with closed-ended lumens because the inner wall of the blood vein can block the side portal and thereby impede blood flow to a degree sufficient to damage the blood sample.

Alternatively, the fibrin component of blood can begin forming a fibrin sheath. This can lead to the formation of a thrombus on or around the indwelling catheter, which would block the side portal and prevent aspiration.

Based on the foregoing, there is a need for a catheter that has good infusion rates for each lumen, allows one lumen to remain dedicated for as long as needed, and assures that a proximal lumen can always be used for blood draws.

SUMMARY OF THE INVENTION

The present invention is directed to a vascular catheter that allows safe use of the lumen with a side effusion portal for blood draws. To this end, a vascular catheter with an expanding side portal has a cylindrical outer tubing housing one or more lumens. The effusion portal is roughly oval-shaped, with one end of the oval joined to a slit in a manner that allows the slit to expand from a closed position to an open position. Preferably, the slit and oval parts of the portal are of roughly equal length. Advantageously, the catheter includes a pair of lumens and one lumen may terminate at the effusion portal.

Accordingly, it is an object of the present invention to provide a catheter with an expanding side portal that allows infusion of blood into the lumen even if the catheter lies near a vessel wall. Other and further objects and advantages of the present invention will appear hereinafter.

BRIEF DESCRIPTION OF THE DRAWINGS

FIG. 2 is a cross-sectional side view of a dual lumen catheter.

FIG. 3 is a side view of the catheter of FIG. 2.

FIG. 4 is a distal end view of the catheter of FIG. 2.

FIG. 5 is a side view of a portal, shown in the closed position.

FIG. 6 is a side view of the portal of FIG. 5 in the open or expanded position.

DETAILED DESCRIPTION OF THE PREFERRED EMBODIMENT

Figure 1:
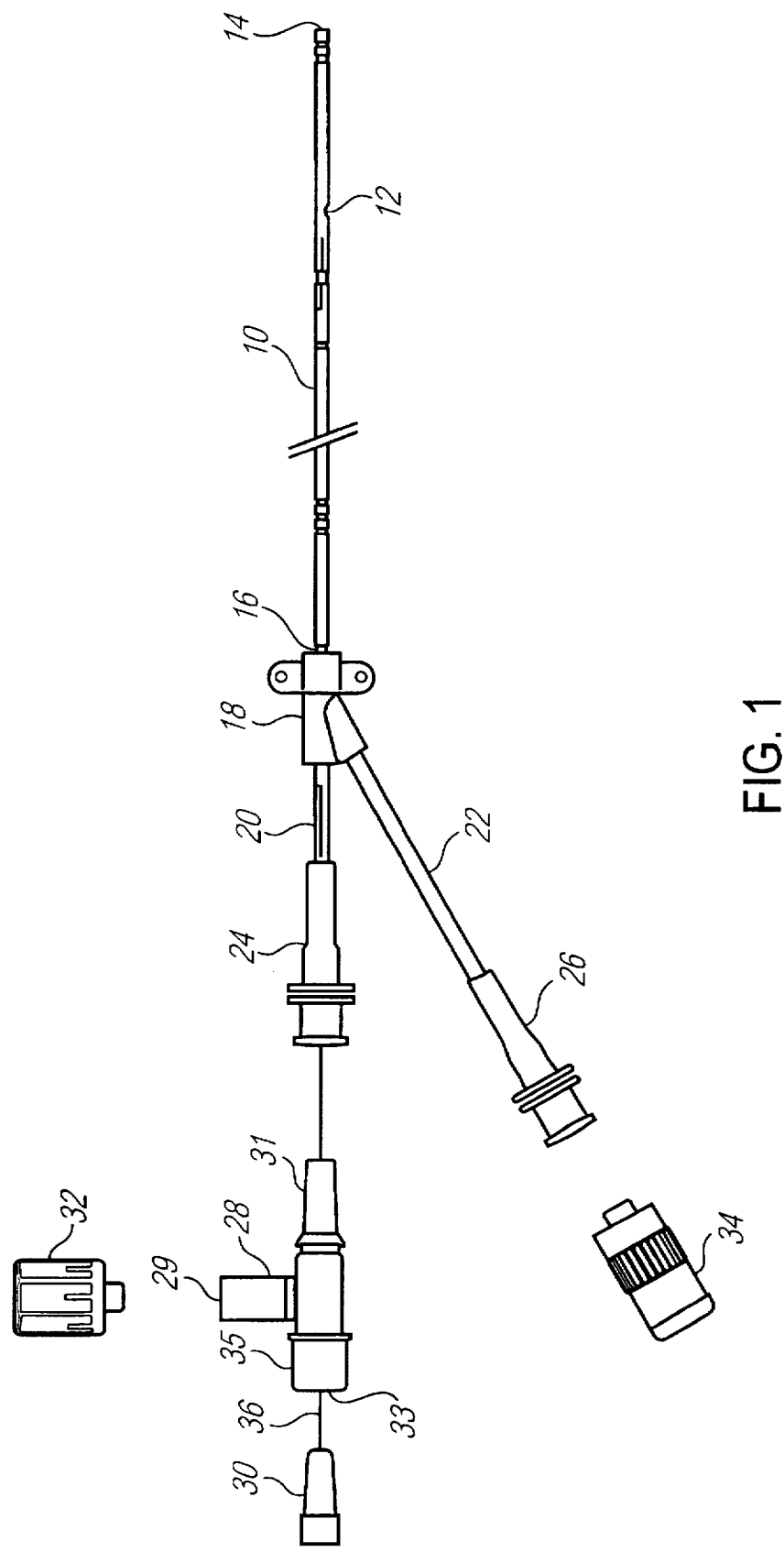
FIG. 1 is a side view of an apparatus for accessing the vascular system of a patient using a dual lumen vascular catheter.

Turning in detail to the drawings, FIG. 1 illustrates a an apparatus for accessing the vascular system of a patient. A dual lumen tubing 10 is preferably manufactured from radiopaque biocompatible medical grade silicone rubber. An effusion portal 12 is located on a side of the tubing 10. The tubing 10 also has a distal end 14 and a proximal end 16. The proximal end 16 is attached to a tube connector 18. In a preferred embodiment, the tube connector 18 is molded from a mixture of titanium dioxide and silicon. The tube connector 18 splits into first and second branches 20, 22, thereby allowing two distinct receptacles (not shown) to communicate with the tubing 10—one for each lumen. A distal sleeve 24 comprising a preassembled hub fits onto the first branch 20. A proximal sleeve 26 comprising a preassembled hub fits onto the second branch 22. In a preferred embodiment, the distal sleeve 24 is blue and the proximal sleeve 26 is white, which aids the practitioner in identifying the use for the particular sleeve. As shown in the preferred embodiment of FIG. 1, a gamma stable T-adaptor or flushing connector 28 is inserted into the preassembled hub of the distal sleeve 24. The T-adaptor 28 comprises an inlet port 33, an outlet port 31, and a flushing port 29. The flushing port 29 can comprise a luer connector. A luer plug 32 can be placed over the flushing port 29. A guidewire 36 having a handle 30 passes through a reclosable septum 35 disposed on the insertion port 33. The guidewire 36 stiffens the tubing 10 during catheter introduction. The resilient nature of the rubber reclosable septum 35 is such that a water-tight seal is formed around the guidewire 36. The guidewire 36 then travels through the T-adapter 28, through the preassembled hub of the distal sleeve 24, through the first branch 20, and into the tubing 10. When completely inserted, the guidewire handle 30 rests against the reclosable septum 35. In addition, a luer injector cap 34 can be connected to the proximal sleeve 26.

With reference to FIGS. 2–4, a dual lumen vascular catheter 38 using the teachings of the present invention is depicted. As shown in FIGS. 2 and 4, a catheter 38 comprises an outer tubing 10 enclosing first and second lumens 40, 42, also known as proximal and distal lumens, respectively. The tubing 10 has distal and proximal ends 14 and 16, respectively. In a preferred embodiment, the catheter 38 is made of a radiopaque, medical-grade, biocompatible silicone rubber material. In an especially preferred embodiment, the wall of the last (most distal) two centimeters of the catheter 38 is made more radiopaque by the addition of tungsten to the silicone rubber elastomer. This mixture may also be doped with additional tungsten. This design not only enhances the radiopaqueness of the tip of the catheter 38, but also adds to the safety and effectiveness of the device by giving the user extra indication of proper placement before infusion commences. The tip also facilitates location of the catheter 38 in the event of malposition of the catheter 38.

Preferably, as shown in FIG. 4, the first and second lumens 40, 42 have D-shaped circumferences of roughly equal length. This design maximizes cross-sectional area for both lumens 40, 42 in the cylindrical tubing 10, thereby ensuring sufficient cross-sectional area to enable free flow of blood in each lumen. Thus, a preferred catheter 38 embodying features of the present invention has the advantage of equally sized lumens 40, 42, allowing good infusion rates for each lumen and making both lumens available for drawing blood samples if necessary.

An effusion portal 12 is located on a side of the tubing 10 as shown in FIG. 3. The effusion portal 12 provides an outlet for the proximal lumen 40. The effusion portal 12 includes an axially oriented, oval-shaped opening 44 and an axially oriented slit 46 in communication therewith. The slit 46 is disposed between the distal end 14 of the tubing 10 and the oval-shaped opening 44. In a preferred embodiment, the opening 44 and slit 46 are of equal length. The distal lumen 42 ends at a portal (not shown) located at the distal end 14 of the tubing 10. Thus, the ends of the proximal and distal lumens 40, 42 are staggered and separated by sufficient space to allow for the simultaneous infusion of incompatible drugs without premature mixing.

FIGS. 5-6 depict an expandable side effusion portal in accordance with the present invention. The portal 12 can expand in the manner shown from the closed position of FIG. 5 to the open position of FIG. 6. As shown, the slit 46 opens at an end in communication with an edge of the oval-shaped opening 44. This enables blood to flow freely through the portal 12 and into the lumen 40 as represented by the arrows in FIG. 6. The expansion of the portal 12 serves to break any vacuum created due to malpositioning of the catheter 38 or fibrin sheath presence. The resultant enlarged portal 12 allows for restored free flow in the proximal lumen 40. Thus, the design renders the proximal side portal viable as a blood sampling port no matter how it is positioned in the vein.

In operation, the apparatus of FIG. 1 serves to deliver medical infusates to the vascular system of a patient, or to provide a means of monitoring the patient's vascular system. Additionally, the apparatus can be used to draw blood samples from the patient. Typical candidates can be either adult or pediatric patients, and include people who require intravenous therapy for more than seven days, hyperalimentation, chemotherapy, continuous narcotic infusion, infusion of hyperosmolar solutions, or long-term intravenous rehydration.

The catheter 38 can be introduced into the vascular system by a variety of methods, including but not limited to using an over-the-needle peel-away introducer or a breakaway introducer. For example, the guidewire 36 can be inserted into a vein via a small needle (not shown) and a splittable sheath/introducer assembly (also not shown) is passed along the guidewire 36 and into the vein. Alternatively, the entire assembly is installed in the patient at once, the catheter 38 including the guidewire 36 preinstalled therein. After catheter 38 intrduction, the guidewire 36 and introducer are removed, leaving the splittable sheath in position in the vein for catheter 38 access. In a preferred embodiment, the guidewire 36 not only adds stiffness to the catheter 38 to facilitate insertion, but can also be used as part of a flushing system to flush the catheter 38 with saline solution during insertion.

This acts as a lubricant to aid in removal of the guidewire 36 once the catheter 38 is properly positioned.

The catheter 38 is generally inserted into the basilic or cephalic veins from the antecubital area of the patient's arm. In a preferred embodiment, securement wings can be provided integral to the construction to anchor the catheter 38 to the skin. Additionally, the tubing 10 can be emblazoned with position marks at five-centimeter intervals to communicate depth of insertion to the user. Preferably, the distal lumen 42 is used for ongoing monitoring or delivery of infusates. Thus, the distal end 14 is most advantageously placed in the superior vena cava where infusates are quickly diluted. The proximal lumen 40 is then available for taking blood samples.

Blood is drawn into the proximal lumen 40 through the side portal 12. When the side effusion portal 12 is blocked by the inner wall of the vein, negative pressure can be applied by a syringe to cause the slit 46 to expand as shown in FIG. 6. The expansion allows free blood flow by relieving the vacuum created between the portal 12 and the wall of the vein.

Thus, a dual lumen catheter is disclosed which employs an expanding side portal to safely draw blood. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A vascular catheter, comprising:
a generally cylindrical tubing comprising a distal end and defining at least one lumen, said tubing defining a portal located on a side of said tubing, said portal comprising an axially oriented opening having a distal end and an axially oriented slit having a proximal end in communication with said opening, said axially oriented slit extending from said distal end of said opening toward said distal end of said tubing, said proximal end of said slit expandable from a closed position to an open position.

2. The catheter of claim 1, wherein said at least one lumen comprises a first lumen and a second lumen, said first lumen having an end connected to said portal.

3. The catheter of claim 2, wherein said first lumen and said second lumen are of approximately equal, D-shaped circumference.

4. The catheter of claim 2, wherein the first lumen comprises a wall, said wall of said first lumen contains a mixture of tungsten and silicone rubber which extends from said distal end of said tubing to a point adjacent said portal and opposing said slit.

5. The catheter of claim 4, wherein said mixture is doped with additional tungsten for a length of approximately two centimeters extending from said distal end of said tubing to a point adjacent said portal and opposing said slit.

6. The catheter of claim 2, further comprising a flushable guidewire to stiffen the catheter to facilitate insertion.

7. The catheter of claim 2, wherein said tubing is made of radiopaque biocompatible medical grade silicone rubber.

8. The catheter of claim 1, wherein said opening and said slit are of equal length.

9. The catheter of claim 1, wherein said axially oriented opening is oval-shaped.

10. A dual lumen vascular catheter, comprising:

a cylindrical tubing comprising a distal end and defining a first lumen and a second lumen, said tubing defining a portal located on a side of said tubing, said portal communicating with said first lumen, said portal comprising an axially oriented opening having a distal end and an axially oriented slit having a proximal end in communication with said opening, said axially oriented slit extending from said distal end of said opening toward said distal end of said tubing, said proximal end of said slit expandable from a closed position to an open position.

11. The catheter of claim 10, wherein said axially oriented opening is oval-shaped.

12. An apparatus for accessing the vascular system of a patient, comprising:

a generally cylindrical tubing comprising a distal end and defining at least one lumen, said tubing defining a portal located on a side of said tubing, said portal comprising an axially oriented opening having a distal end and an axially oriented slit having a proximal end in communication with said opening, said axially oriented slit extending from said distal end of said opening toward said distal end of said tubing, said proximal end of said slit expandable from a closed position to an open position;

a tube connector attached to said generally cylindrical tubing opposite said distal end, said tube connector comprising at least one branch in communication with said at least one lumen; and means for delivering fluid to, or removing fluid from, said at least one branch.

13. The apparatus of claim 12 wherein said at least one lumen comprises first and second lumens and said at least one branch comprises first and second branches.

14. The catheter of claim 12, wherein said axially oriented opening is oval-shaped.

* * * * *